United States Patent [19]

Takeo et al.

[11] 4,159,345

[45] Jun. 26, 1979

[54] NOVEL EXCIPIENT AND PHARMACEUTICAL COMPOSITION CONTAINING THE SAME

[75] Inventors: Kimihiko Takeo; Tetuya Aoyagi; Akimitsu Tamada, all of Nobeoka, Japan

[73] Assignee: FMC Corporation, Philadelphia, Pa.

[21] Appl. No.: 873,990

[22] Filed: Jan. 31, 1978

[30] Foreign Application Priority Data

Apr. 13, 1977 [JP] Japan ................................ 52-41545
Jul. 12, 1977 [JP] Japan ................................ 52-82548

[51] Int. Cl.$^2$ .............................................. A61K 47/00
[52] U.S. Cl. ...................................................... 424/362
[58] Field of Search ......................................... 424/362

[56] References Cited

U.S. PATENT DOCUMENTS

| | | | |
|---|---|---|---|
| 3,146,168 | 8/1964 | Battista | 424/362 X |
| 3,966,899 | 6/1976 | Nakai et al. | 424/19 |
| 4,001,434 | 1/1977 | Nakai et al. | 424/361 |

OTHER PUBLICATIONS

Bolhuis et al. Pharmaceutisch Weekblad 108(22): 469–481, Jun. 1973.

*Primary Examiner*—Shep K. Rose
*Attorney, Agent, or Firm*—Charles H. Johnson

[57] ABSTRACT

An excipient for use in manufacture of tablets, capsules, powders, microgranules and granules which consists essentially of a microcrystalline cellulose having an average degree of polymerization of 60 to 375 and obtained through acid hydrolysis or alkaline oxidative degradation of a celulosic substance selected from linters, pulps and regenerated fibers, said microcrystalline cellulose being a white cellulosic powder having an apparent specific volume of 1.6 to 3.1 cc/g, a repose angle of 35° to 42°, a 200-mesh sieve residue of 2 to 80% by weight and a tapping apparent specific volume of at least 1.4 cc/g and a pharmaceutical composition comprising a pharmaceutically active ingredient and the excipient. This excipient has improved flowability and moldability or compressibility whereby excellent pharmaceutical preparations may be easily provided. In addition, pharmaceutical compositions obtained using such excipient are excellent in various pharmaceutical characteristics such as rate of disintegration, rate of dissolution, etc.

10 Claims, No Drawings

NOVEL EXCIPIENT AND PHARMACEUTICAL COMPOSITION CONTAINING THE SAME

The present invention relates to a pharmaceutical excipient for use in manufacture of tablets, capsules, powders, microgranules and granules.

More specifically, when the excipient of the present invention is used for manufacture of tablets, it permits high-speed direct compression and provides tablets in which the unevenness of the weight of the main ingredient content is remarkably reduced and which have an increased rate of disintegration and an improved rate of dissolution of the main ingredient.

When the excipient of the present invention is used for manufacture of capsules, it exerts effects of improving the homogeneousness in a powdery mix to be encapsulated, increasing the speed of mixing the ingredients, reducing the unevenness of the filled weight of the powdery mix in resulting capsules and increasing quantities of the powdery mix when encapsulated, shortening the disintegration time of the resulting capsules and preventing prolongation of the disintegration time of the resulting capsules which prolongation is caused with the lapse of time.

When the excipient of the present invention is used for manufacture of powders, it provides powders in which the uneven distribution of the main ingredient is reduced remarkably and the flowability of a powdery mix is enhanced and which are excellent in the adaptability to the packeting operation and can be taken with ease.

When the excipient of the present invention is used for manufacture of microgranules and granules, it can reduce the necessary amount of a binder at the step of wet granulation and improve the strength of the resulting particles or granules even with the reduced quantity of the binder while effectively preventing dusting of microgranules or granules, and it can provide particles and granules having excellent disintegrating characteristics in high yields.

Further, the present invention relates to a pharmaceutical composition for tablets, capsules, powders, microgranules or granules, which comprises an excipient having novel powder characteristics as a binder or disintegrating agent, and a main pharmaceutical ingredient and other pharmaceutical additives.

Conventional solid pharmaceutical compositions generally comprise (i) a main ingredient (pharmaceutically active ingredient), (ii) an excipient, (iii) a binder, (iv) a disintegrating agent and (v) other additives.

As the excipient, there have been used various substances such as lactose, starches, calcium phosphate and glucose. Methyl cellulose (MC), hydroxypropyl cellulose (HPC), polyvinyl pyrrolidone (PVP), microcrystalline cellulose and the like have been used as the binder. As the disintegrating agent, there have been used starches, calcium carboxymethyl cellulose (CMC-Ca), ion exchange resins and the like. These substances have merits and demerits in properties thereof, and therefore, none of them can be used as versatile additives effective as an excipient, a binder and a disintegrating agent concurrently.

For example, lactose, a typical instance of the excipient suitable for direct compressing has a high apparent density close to that of a main ingredient and it has a very good flowability if it is crystalline. However, lactose is very poor in the moldability or compressibility and tablets formed by using lactose as an excipient cannot be practically applied. Also starch is poor in the moldability or compressability when it is used alone. Each of MC, HPC and PVP, that have been used as binders, shows a sufficient effect as an excipient in the direct compression when used in a large quantity and has a sufficient moldability or compressibility. Each of these binders, however, is poor in flowability and is highly swollen on absorption of water so that in tablets formed by using MC, HPC or PVP, the stability is degraded with the lapse of time. If the moldability is enhanced so as to improve the strength of tablets, the disintegration time is inevitably prolonged. A conventional disintegrating agent such as CMC-Ca or an ion exchange resin is poor in the moldability or compressibility. In general, an ion exchange resin per se has a good flowability but its flow characteristics are insufficient for improving the flowability of a pharmaceutical composition comprising a large quantity of a main ingredient and other additives. Finely divided silica is effective for improving the flowability, but if this flow modifier is incorporated in a large quantity, such undesirable phenomena as capping and sticking are readily caused to occur at the tableting step and the bulk of a powdery mix is undesirably increased. An inorganic excipient such as calcium phosphate has a good flowability and a high apparent density, but capping is readily caused when the direct compression operation is carried out at a high speed. Further, since the excipient is composed of an inorganic substance, main parts of a tablet compressing machine, such as a die and a punch, are readily worn. Accordingly, use of such inorganic excipient is not preferred from the practical viewpoint.

A high-speed direct compression machine has recently been developed for enhancing the productivity, but the excellent capacities of this newly developed high-speed direct compressing machine cannot be sufficiently exerted because of such defects of conventional excipients as (i) poor flowability, (ii) high bulk, (iii) insufficient strength if the compression time is short, and (v) generation of large quantities of dusts.

Recently, the effectiveness and reliability of medicines are strictly evaluated and checked, and efforts have been intensively made to (i) reduce the weight unevenness in tablets and (ii) eliminate the unevenness of the main ingredient content in tablets. These objects will be attained if there is found an excipient having a high apparent density and an excellent flowability and such excipient is incorporated into a pharmaceutically active ingredient (often referred to as "main ingredient"). However, an excipient suitable for direct compression meeting these requirements satisfactorily has not been developed in the art.

Under such background, it has been eagerly desired in the art to develop a novel excipient having a high moldability or compressibility, a small bulk (high apparent density) and a good flowability and being capable of increasing a rate of disintegration and accelerating dissolution of the main ingredient, which is applicable to the wet method as well as the dry method in preparation of pharmaceutical products and which has well-balanced general properties.

It is therefore a primary object of the present invention to provide a novel excipient having a high moldability or compressibility, a small bulk and a good flowability and providing tablets and capsules in which the unevenness of the weight and the unevenness of the main ingredient content are remarkably reduced, especially easily-disintegratable tablets according to the direct compression method.

Another object of the present invention is to provide an excipient useful for manufacture of powders, microgranules, granules, and tablets according to the method of compression with wet granulation.

Still another object of the present invention is to provide a pharmaceutical composition which makes it possible to manufacture tablets, capsules, powders, microgranules and granules having high quality.

In accordance with the present invention, the foregoing and other objects can be attained by an excipient consisting essentially of a microcrystalline cellulose having an average degree of polymerization of 60 to 375 and obtained through acid hydrolysis or alkaline oxidative degradation of a cellulosic substance selected from linters, pulps and regenerated fibers, microcrystalline cellulose being a white cellulosic powder having an apparent specific volume of 1.6 to 3.1 cc/g, a repose angle of 35° to 42°, a 200-mesh sieve residue of 2 to 80% by weight and a tapping apparent specific volume of at least 1.4 cc/g.

This white cellulosic powder is prepared, for example, according to the following method.

Refined linters are hydrolyzed at 125° C. for 150 minutes in a 0.7% aqueous solution of hydrochloric acid, and the hydrolysis residue is neutralized, washed and filtered to obtain a wet filter cake. The cake is sufficiently pulverized in a kneader, and ethanol in a volume larger than the volume of the pulverized cake is added to the pulverized cake. The mixture is compressed and filtered, and the residue is air-dried. The resulting cellulose powder mass is finely pulverized by a hammer mill and passed through a 40-mesh sieve to obtain a cellulosic powder having a degree of polymerization of 180, an apparent specific volume of 2.0 cc/g, a repose angle of 40°, a 200-mesh sieve residue of 12% by weight and a tapping apparent specific volume of 1.6 cc/g.

Of course, it must be noted that the method for preparing the microcrystalline cellulosic powder of the present invention is not limited to the above-mentioned method and the microcrystalline cellulosic powder of the present invention is not limited to products obtained according to the above-mentioned method.

In order for an excipient to have a moldability sufficient for forming tablets according to the direct compression method, it is important that the excipient should have an average degree of polymerization (hereinafter referred to as "DP") in the range of from 60 to 375. If DP is lower than 60, the moldability is insufficient and provides a powdery mix in which capping tends to readily occur in the direct compression. Accordingly, use of an excipient having such a low DP value is not preferred from the practical viewpoint. If DP is higher than 375, fibrous characteristics are manifeste in the excipient and the requirements of the flowability and bulk density (apparent specific volume) described in detail hereinafter are not satisfied.

The excipient should have an apparent specific volume of 1.6 to 3.1 cc/g as determined according to the method described hereinafter. If the apparent specific volume is larger than 3.1 cc/g, the bulk of the resulting powder mix is large and it is not suitable for high-speed direct compression. If the apparent specific volume is smaller than 1.6 cc/g, the specific gravity is close to that of the main ingredient but the resulting powder mix is too compact and the quantity of plastic deformation at the step of compression molding is too small. Further, in this case, entanglements of granules are reduced and the resulting powdery mix becomes poor in the moldability with increased tendency to cause capping.

The excipient should also have a repose angle of 35° to 42° as measured according to the conical deposition method. The repose angle is one of factors determining flow characteristics of powder. In case of microcrystalline cellulose having a repose angle smaller than 35°, the flowability of the resulting powdery mix is indeed improved remarkably and the powdery mix flows smoothly from a hopper, but because of too high flowability of the microcrystalline cellulose, separation and/or segregation of the ingredients is caused in the hopper and no substantial effect of reducing the unevenness of the main ingredient content can be attained. When the repose angle exceeds 42°, the flowability becomes insufficient and bridging is caused in the powdery mix in the hopper, and therefore, flow-out of the powdery mix from the hopper is inhibited, weight variations in tablets become conspicuous and high-speed direct compression is impossible.

The particle size of microcrystalline cellulose should be such that the content of the 200-mesh sieve residue is 2 to 80% by weight as determined according to the sieve analysis method. When microcrystalline cellulose having a 200-mesh sieve residue of lower than 2% by weight is used as an excipient the flowability of the resulting powdery mix is poor and the requirement of the repose angle of at least 42° is not satisfied in this microcrystalline cellulose. Further, generation of dusts is conspicuous at the tableting step. If the 200-mesh sieve residue exceeds 80% by weight, the particle is coarse and the flowability is enhanced, but the adaptability to the compression molding is degraded.

If the tapping apparent specific volume is lower than 1.40 cc/g, the moldability of the resulting powdery mix is insufficient. The upper limit of the tapping apparent density is naturally defined by the upper limit of the apparent specific volume of 3.1 cc/g. If the tapping apparent density is not higher than this value, no particular trouble or disadvantage is brought about.

A capsule is one of typical pharmaceutical preparations as well as a tablet. Also in the field of manufacture of capsules, a high-speed encapsulating machine has been developed for improving the productivity. However, since there is not an excellent encapsulation additive matchable with the capacity of the machine, the capacity of this machine is not sufficiently exerted. This is due mainly to insufficient flowability of a powdery mix to be encapsulated.

Large capsules give an unpleasant feeling when they are orally administered and smaller capsules are preferred, and reduction of the size in capsules is desired also by manufactures and dealers because reduction of the size in capsules results in enhancement of the productivity, rationalization of packaging costs and reduction of transportation costs. However, in actuality, reduction of the size in capsules involves various difficulties, which are concerned with such properties of powdery mixes to be encapsulated as (i) the bulk (apparent specific volume), (ii) flowability, (iii) particle size, (iv) surface characteristics and (v) compressibility.

In case of an encapsulating machine as in other medicine manufacturing machines treating powders, the quantity of powder to be encapsulated is expressed by the volume rather than by the weight. Accordingly, in general, as the bulk of powder is small, a unit weight of powder to be encapsulated is increased and the size of capsules can be reduced. The encapsulating machine includes various types, for example, an auger type, a disc type and a compressing type. The flowability of powder is very important irrespective of the type of the encapsulating machine. For example, in case of an auger type machine, powder should be smoothly filled in capsules with movement of an auger, and in case of a disc type machine, powder should be smoothly filled in capsules by free flow owing to its own weight. Further, in case of a compressing type machine, powder should be smoothly and completely filled with nozzles in holes formed by punching. As is seen from the foregoing illustration, the flowability of powder is very important in any of encapsulating methods. Also the particle size of powder is important. In case of an auger type machine, too fine powder grates a screw and the flowability is degraded. Further, in case of a compressing type machine, too fine powder leaks out from a spacing between a nozzle and a spindle and adheres to them, and therefore, friction heat is generated by the vertical movement of the spindle and it is impossible to continue the operation for a long time. Too coarse particles fall down from a nozzle during the filling operation in case of a compressing type machine, resulting in unevenness of the filled weight. The compressibility of powder is especially important in case of a compressing type machine, and if the compressibility is insufficient, the filled weight is uneven in resulting capsules.

In addition to the foregoing problems involved in the manufacturing equipments, there is another problem important from the pharmaceutical viewpoint. More specifically, when a powdery mix to be encapsulated is prepared, it is necessary to mix the respective ingredients as homogeneously as possible. Even when the same weight of the powdery mix is filled in the respective capsules, if the content of the pharmaceutically active ingredient (main ingredient) is not uniform in the powdery mix, the uniformity of the filled weight becomes insignificant. Accordingly, it is very important to increasing the mixing speed and attain homogeneousness in the resulting powdery mix.

As-prepared capsules are disintegrated in a short time and are excellent in the availability. However, if they are allowed to stand still for a long time, moisture permeates into capsules through gelatin walls and the filled powder adsorbs water or is caked or solidified, and as a result, the disintegration time is prolonged. This difference of the disintegration time between as-prepared capsules and capsules allowed to stand still for a long time will result in the difference of availability of capsules as medicinal products and hence, should be eliminated.

Influences of powder characteristics of microcrystalline cellulose as the excipient on capsules will now be described.

When the apparent specific volume of powder is larger than 3.1 cc/g, the flowability is degraded and the bulk is increased, and it is impossible to increase the unit weight to be encapsulated. If the apparent specific volume is smaller than 1.6 cc/g, it is possible to increase the filled weight and enhance the flowability, but compressibility is substantially lost in the resulting powder mix. Accordingly, in order to attain high flowability and high compressibility and increase the filled weight, it is necessary that the apparent specific volume of powder should be in the range of from 1.6 to 3.1 cc/g.

If the repose angle of powder is larger than 42°, the flowability of the powdery mix to be encapsulated is degraded and the unevenness of the filled weight becomes conspicuous. Further, the filling easiness of the powdery mix is degraded and it is impossible to increase the unit weight to be encapsulated.

The particle size of powder should be such that the 200-mesh sieve residue is 2 to 80% by weight. When the 200-mesh sieve residue exceeds 80% by weight, in case of a compressing type encapsulating machine, no good compressibility is manifested, and leakage of powder from a nozzle becomes conspicuous, resulting in increase of the unevenness of the filled weight. In case of a disc type encapsulating machine, when the powdery mix is shaken by a vibrator, separation of the excipient powder from the main ingredient is caused. When the 200-mesh sieve residue is lower than 2% by weight, troubles are caused due to too fine a particle size. For example, in case of a disc type encapsulating machine, powder is filled in a spacing between a capsule and a disc and smooth disposal of capsules becomes impossible. In case of a compressing type encapsulating machine, powder is filled in a spacing between a spindle and a nozzle and smooth vertical movement of the spindle becomes impossible, and the unevenness of the filled weight becomes conspicuous.

A good compressibility necessary for encapsulation according to a compressing type machine is not attained when the tapping apparent specific volume is smaller than 1.4 cc/g, and in this case, it is necessary to elevate the compression pressure and the disintegration time of resulting capsules becomes too long. From the viewpoint of the filling easiness, there is no upper limit of the tapping apparent specific volume, and if other powder characteristics are selected in optimum ranges, the upper limit of the tapping apparent specific volume will naturally be determined. In general, the upper limit of the tapping apparent specific volume is about 2.6 cc/g.

When the excipient of the present invention is applied to powders, the packeting operation can be facilitated because the excipient gives good flowability and bulk to the powdery mix. Further, at the powder preparing step, the excipient of the present invention shows a good compatibility with the pharmaceutically active ingredient (main ingredient) and other excipient and additives, and the main ingredient can be uniformly distributed in the powdery mix by short-time mixing. Moreover, even if the powdery mix is subjected to a long-period storage test, agglomeration or caking is not caused but a dry and incohesive state is maintained in the powdery mix. These advantages attained by application of the excipient of the present invention to powders are especially conspicuous when microcrystalline cellulose having an apparent specific volume of 1.6 to 3.1 cc/g, a repose angle of 35° to 42°, preferably 38° to 41°, and a 200-mesh sieve residue of 2 to 80% by weight, preferably 5 to 40% by weight, is used as the excipient.

Another prominent feature of the excipient of the present invention is that when the excipient of the present invention is applied to the wet granulation method (namely, final products are tablets according to the method of compression with wet granulation, microgranules, granules, and granule-filled capsules), granulation is possible with a reduced amount of a binder, the strength of granules is increased while preventing dusting, and the fatal defect of conventional cellulosic excipients, namely poor disintegrating property, can be overcome and the disintegrating property of tablets and granules can be greatly improved. These effects are manifested conspicuously especially when the average degree of polymerization of microcrystalline cellulose aggregates is 60 to 375, especially 70 to 180, and the 200-mesh sieve residue is 2 to 80% by weight, preferably 10 to 30% by weight. The apparent specific volume has an influence on the amount of a binder necessary for granulation. As the apparent specific volume of microcrystalline cellulose is small, granulation is possible with a small amount of a binder, but in order to attain good strength and disintegrating property in granules, it is preferred that the apparent specific volume of microcrystalline cellulose is 1.6 to 3.1 cc/g, especially 1.9 to 2.8 cc/g.

When tablets are prepared according to the direct compression method, a pharmaceutical composition to be tableted comprises a main ingredient, an excipient, a binder and a disintegrating agent, and mutual relations among these ingredients cannot be neglected. For example, when the flowability of the main ingredient is extremely poor, if the concentration of the main ingredient exceeds a certain level, the flowability of the powdery mix is drastically reduced, and direct compression becomes difficult or the weight of the main ingredient content becomes extremely uneven in the resulting tablets. When the repose angle, which is one factor useful for evaluating the flowability of powder, is larger than 50° with respect to a main ingredient used, if the main ingredient content exceeds 65% by weight based on the pharmaceutical composition, the repose angle of the pharmaceutical composition exceeds 47° even by using microcrystalline cellulose (excipient) of the present invention if the excipient content is lower than 15% by weight based on the composition, and it is impossible to feed smoothly the powdery mix by using an oven, a feed chute or the like, resulting in increase of the unevenness of the tablet weight or main ingredient content. When the content of the above main ingredient is lower than 65% by weight based on the composition, good results are obtainable when microcrystalline cellulose of the present invention is incorporated in an amount of 15% by weight or less based on the composition. However, in this case, if the content of microcrystalline cellulose of the present invention is lower than 10% by weight based on the composition, the practical strength of resulting tablets is not increased and the disintegration time of the tablets is long. Thus, it has been found that microcrystalline cellulose of the present invention should be incorporated in an amount of at least 10% by weight based on the composition. On the other hand, when a main ingredient having a repose angle smaller than 50° and a relatively good flowability is used, even if the main ingredient content exceeds 80% by weight based on the composition, a good flowability can be maintained in the powdery mix in a hopper. Also in this case, however, it is necessary that microcrystalline cellulose of the present invention should be incorporated in an amount of at least 10% by weight based on the composition.

In the manufacture of capsules and powders where powder is directly subjected to a molding operation as in case of the direct compression method, from the viewpoints of the flowability in a hopper and the uniformity of the filled weight or packeted weight, conditions described above with respect to the tablet compressing method should similarly be satisfied. Namely, when a main ingredient having a repose angle larger than 50° is used in an amount larger than 65% by weight based on the composition, in order to attain a good flowability in the powdery mix, it is necessary that microcrystalline cellulose of the present invention should be incorporated in an amount of at least 15% by weight based on the composition. When the content of the above ingredient is lower than 65% by weight based on the composition or when the repose angle of the main ingredient is smaller than 50°, if microcrystalline cellulose of the present invention is incorporated in an amount of 10% by weight based on the composition, good flowability, filling property and compression moldability can be maintained.

Tablets and capsules obtained by using the pharmaceutical composition of the present invention are characterized by a short disintegration time, a storage stability and a high speed of dissolution of the main ingredient.

Effects attained when the pharmaceutical composition of the present invention is applied to the manufacture of granules, fine particles and tablets through the wet granulation step will now be described.

First of all, there can be mentioned an advantage that the resulting granules or tablets disintegrate very promptly. In addition, the adaptability to extrusion granulation can be remarkably improved and the strength of resulting granules and tablets is increased and dusting can be reduced. In conventional processes for the manufacture of granules or microgranules, in order to reduce the dusting and obtain products excellent in strength, it is necessary to increase the amount of a binder incorporated but this results in a fatal defect of a long disintegration time. In view of this fact, it will readily be understood that the present invention is highly progressive over the conventional techniques.

The foregoing effects attained by the pharmaceutical composition of the present invention for manufactures of granules, microgranules and tablets according to the wet method are advantageously obtained when microcrystalline cellulose of the present invention is incorporated in an amount of 1 to 50% by weight, preferably 2 to 40% by weight based on the composition.

The pharmaceutical composition of the present invention may be formed into medicinal products according to any of conventional processes for the manufacture of solid medicines. More specifically, microcrystalline cellulose of the present invention is incorporated into at least one main ingredient, other additives are added according to need, and the resulting composition is molded into tablets, pills and granules according to a known wet or dry method. For example, when tablets are prepared according to the method of compression with wet granulation, microcrystalline cellulose may be incorporated afterwards. Further, capsules and powders can be prepared from the pharmaceutical composition of the present invention according to known methods.

Further, film- or sugar-coated tablets may optionally be prepared by coating tablets of the pharmaceutical composition of the present invention with a film or sugar. It also is possible to pulverize tablets once prepared according to the present invention, mix the resulting powder with other main ingredient, excipient, disintegrating agent, colorant, lubricant and like additives and mold the mixture into tablets again. Still further, a syrup may be prepared by dispersing and suspending the pharmaceutical composition of the present invention in an appropriate dispersion medium.

Powder characteristics mentioned in the instant specification and appended claims are those determined according to the following methods.

Sieving:

A sample (50 g) is sieved and classified for 20 minutes by using a JIS standard sieve attached to a low-tap type sieving and shaking machine manufactured by Yanagimoto Seisakusho, Japan and the particle size distribution and average particle size of the sample are determined according to this method.

Apparent specific volume:

A value determined by using a powder tester Model PT-D manufactured by Hosokawa Funtai Kogaku Kenkyusho, Japan.

Tapping apparent specific volume:

A value obtained when 50 g of a sample powder is charged in a Tap Denser KYT-1000 manufactured by Seishin Kigyo K. K. and the charged powder is tapped until the equilibrium state is attained.

Degree of polymerization:

A value determined according to the cuprammonium solution viscosity-measuring method specified by JIS.

Repose angle:

A value determined according to the conical deposition method using a powder tester Model PT-D manufactured by Hosokawa Funtai Kogaku Kenkyusho.

The present invention will now be described in detail by reference to the following Examples that by no means limit the scope of the invention.

EXAMPLE 1

Commercially available dissolving pulp (1 Kg) was finely divided and hydrolyzed in a 10% aqueous solution of hydrochloric acid at 105° C. for 20 minutes. The acid-insoluble residue was recovered by filtration, washed, air-dried and pulverized by an ordinary hammer mill. The pulverized product was passed through a 50-mesh sieve to remove coarse particles and obtain 600 g of microcrystalline cellulose (A) having an average particle size of 35μ, a whiteness of 90, DP of 180, an apparent specific volume of 2.78 cc/g, a tapping apparent specific volume of 1.90 cc/g, a 200-mesh sieve residue of 22% by weight and a repose angle of 41°.

Commercially available dissolving pulp (1 Kg) was finely divided and hydrolyzed in a 1% aqueous solution of sulfuric acid at 115° C. under pressure for 35 minutes, and the acid-insoluble residue was recovered by filtration, washed, air-dried and pulverized by a hammer mill. Coarse particles were removed by passing the pulverized product through a 50-mesh sieve to obtain 700 g of microcrystalline cellulose (B) having an average particle size of 35μ, a whiteness of 90, DP of 390, an apparent specific volume of 3.33 cc/g, a tapping apparent specific volume of 2.41 cc/g, a 200-mesh sieve residue of 25% by weight and a repose angle of 47°.

Commercially available kraft pulp (1 Kg) was finely divided and hydrolyzed in a 1% aqueous solution of hydrochloric acid at 120° C. under pressure for 30 minutes, and the acid-insoluble residue was recovered by filtration, washed, air-dried and pulverized by a hammer mill. Coarse particles were removed by passing the pulverized product through a 60-mesh sieve to obtain 650 g of microcrystalline cellulose (C) having an average particle size of 32μ, a whiteness of 92, DP of 130, an apparent specific volume of 1.96 cc/g, a tapping apparent specific volume of 1.58 cc/g, a 200-mesh sieve residue of 17% by weight and a repose angle of 35°.

Rayon yarn waste (1 Kg) was finely divided and hydrolyzed in a 1% aqueous sulfuric acid solution at 105° C. for 120 minutes, and a product (D) was obtained in the same manner as described above with respect to the product (C). The yield was 52%. The product (D) was microcrystalline cellulose having an average particle size of 20μ, a whiteness of 88, DP of 40, an apparent specific volume of 1.40 cc/g, a tapping apparent specific volume of 1.32 cc/g, a 200-mesh sieve residue of 5% by weight and a repose angle was 34°.

In a 5-liter capacity V-blender, 800 g of commercially available pharmacopoeial crystalline ascorbic acid (having a repose angle of 39°), 95 g of commercially available DMV lactose, 100 g of microcrystalline cellulose (A), (B), (C) or (D) and 5 g of magnesium stearate were mixed, and the mixture were compressed and molded into tablets by using a high-speed direct compressing machine (Model RT-S22-T35 manufactured by Kikusui Seisakusho) comprising 12 R punches of 8 mm diameter. The rotation speed of a turn table was 30 rpm. Properties of obtained tablets (each having a weight of 220 mg) are shown in Table 1.

Table 1

| Microcrystalline Cellulose Sample | Repose Angle of Powdery Mix | Tablet Weight Dispersion (n = 20) | Tablet Hardness (n = 20) | Disintegration Time (seconds) |
|---|---|---|---|---|
| A | 39° | 1.1% | 4.0 Kg | <30 |
| B | 43° | 3.0% | 4.2 Kg | 180 |
| C | 36° | 0.8% | 3.9 Kg | <15 |
| D | 36° | 0.8% | capping | — |

The sample B having a large apparent specific volume and a large repose angle was defective in that the weight unevenness was not moderated and the tablet weight dispersion was as high as 3%. In the sample D having low DP and too small an apparent specific volume, the compressibility was low and capping was caused. In each of the samples A and C, the disintegration time was very short.

EXAMPLE 2

Tablets were molded in the same manner as in Example 1 except that the rotation speed of the turn table was changed as indicated in Table 2. The composition of the powdery mix was the same as in Example 1. For comparison, a commercially available excipient (microcrystalline cellulose sold under tradename "Avicel PH-101" and manufactured by F M C Corporation was similarly tested. The tablets were evaluated based on the weight dispersion (average weight=220 mg; n=20). Obtained results are shown in Table 2.

Table 2

| | Weight Dispersion | | | |
|---|---|---|---|---|
| | RPM 20 | RPM 30 | RPM 40 | RPM 50 |
| Sample A | 0.8% | 1.0% | 1.1% | 1.3% |
| Sample B | 2.4% | 3.0% | 5.2% | 7.2% |
| Sample C | 0.8% | 0.8% | 0.9% | 1.2% |
| Sample D | 0.8% | 0.8% | 0.8% | 0.9% |
| Avicel PH-101 | 2.1% | 2.8% | 4.5% | 4.9% |

Notes:
[1] In case of the sample D, capping was caused in each run.
[2] In case of each of the samples A, B and C, the tablet hardness was 3 to 4 Kg in each run.

When the sample B having such a large apparent specific volume of 3.33 cc/g that in order to attain the same filled weight, the depth of the lower punch had to be increased was subjected to high-speed direct compression, the weight unevenness became conspicuous and no good results were obtained. In case of the commercially available excipient (Avicel PH-101), no satisfactory results were obtained because of too large an apparent specific volume (3.3 cc.g).

EXAMPLE 3

Powdery mixes having a composition indicated in Table 3 were prepared by using the same ascorbic acid as used in Example 1 and microcrystalline cellulose samples (A) and (D) obtained in Example 1.

Table 3

| Sample No. | Main Ingredient | Micro-crystalline Cellulose | Powdery Sodium Lauryl Sulfate | Repose Angle of Powdery Mix |
|---|---|---|---|---|
| 1 | 1000 g | 990 g (A) | 10 g | 36° |
| 2 | 1000 g | 990 g (D) | 10 g | 35° |

Continuous direct compression was carried out in the same manner as described in Example 1. In case of sample No. 2, when the molding pressure was elevated, capping was caused. Accordingly, in each run no substantial pressure was applied but the sample was compressed only very lightly. Tablets (having a hardness of about 2 kg) discharged from a discharge opening were sampled at predetermined intervals. The sampled brittle tablets were precisely weighed in a 500 ml-capacity Erlenmeyer flask and 300 ml of pure water was charged therein. The flask was sealed and the charge was shaken for 120 minutes by using a shaker. The content was filtered through a membrane filter having a pore diameter of $0.2\mu$. The filtrate was appropriately diluted, and the absorbance of the diluted extract was measured at a wavelength of 245 nm by using a Shimazu-Baush & Lomb spectrophotometer "Spectronic SSUV" and the main ingredient content was determined according to the calibration method. Obtained results are shown in Table 4. As a result of preliminary experiments, it was confirmed that the recovery was substantially 100%.

Table 4

| Sample No. | Theoretical Value | Main Ingredient Content (%) (average value, n = 5) | | | | |
|---|---|---|---|---|---|---|
| | | At Start | 10 Minutes | 20 Minutes | 30 Minutes | 40 Minutes |
| 1 | 50.0 | 49.7 ($\delta$=0.75) | 49.9 ($\delta$=0.81) | 50.1 ($\delta$=0.70) | 50.1 ($\delta$=0.77) | 49.8 ($\delta$=0.82) |
| 2 | 50.0 | 50.1 ($\delta$=0.91) | 50.5 ($\delta$=1.1) | 52.2 ($\delta$=1.3) | 50.7 ($\delta$=2.2) | 48.3 ($\delta$=3.5) |

As will be apparent from the foregoing data, in case of microcrystalline cellulose having too high a flowability, separation of the ingredients was caused while the powdery mix flowed in a hopper, and in the initial stage, the main ingredient content was close to the theoretical value, but with the lapse of time, the main ingredient content was increased and the unevenness of the main ingredient content become conspicuous, and in the final stage, the main ingredient content was lower than the theoretical value. Thus, it was confirmed that in case of microcrystalline cellulose having too high a flowability, variations of the main ingredient content were conspicuous in resulting tables.

EXAMPLE 4

Refined linters (1 kg) were sufficiently disentangled and hydrolyzed in a 0.8% aqueous solution of hydrochloric acid at 120° C. under pressure for 45 minutes, and the acid-insoluble residue was recovered by filtration, washed, air-dried and pulverized at a rate of 1.3 kg/hr by using a Nara-type free pluverizer (Model M-2). Coarse particles were removed by passing the pulverized product through a 50-mesh sieve to obtain a free-flowing white powder (E) having an average particle size of $32\mu$, DP of 160, an apparent specific volume of 2.3 cc/g, a tapping apparent specific volume of 1.71 cc/g, a repose angle of 39.5° and a 200-mesh sieve residue of 13% by weight.

An air-dried product of hydrolyzed linters obtained under the same conditions as described above was pulverized by a microjet mill pulverizer Model FSS manufactured by Seishin Kigyo K.K., Japan while adjusting the air feed rate and the powder feed rate, to obtain samples (F), (G) and (H) having properties shown in Table 5.

Table 5

| | Sample (F) | Sample (G) | Sample (H) |
|---|---|---|---|
| Apparent specific volume (cc/g) | 3.32 | 2.90 | 1.93 |
| Tapping apparent specific volume (cc/g) | 2.30 | 1.94 | 1.60 |
| Ropose angle (degrees) | 44 | 42 | 45 |
| 200-Mesh sieve residue (% by weight) | 23 | 19 | 1.8 |

Commercially available kraft pulp was finely divided and hydrolyzed in a 2% aqueous solution of sulfuric acid (bath ratio =15) at 125° C. under pressure for a time indicated in Table 6, and the acid-insoluble residue was recovered by filtration, washed, dried for 10 hours by hot air maintained at 60° C. and pulverized by a hammer mill. Coarse particles were removed by passing the pulverized product through a 50-mesh sieve. In this manner, samples (I), (J), (K) and (L) shown in Table 6 were obtained. The degree of pulverization was changed in the samples by changing the speed of the hammer mill and the mesh size of a discharge screen at the pulverizing step.

Table 6

| | Sample (I) | Sample (J) | Sample (K) | Sample (L) |
|---|---|---|---|---|
| Hydrolysis time (minutes) | 5 | 10 | 25 | 80 |
| Apparent specific volume (cc/g) | 3.50 | 3.00 | 2.53 | 1.89 |
| Tapping apparent specific volume (cc/g) | 2.42 | 2.01 | 1.72 | 1.52 |
| Repose angle (degrees) | 45 | 42 | 38 | 43 |
| 200-Mesh sieve residue (% by weight) | 48 | 32 | 15 | <2.0 |

Table 6-continued

|  | Sample (I) | Sample (J) | Sample (K) | Sample (L) |
|---|---|---|---|---|
| DP | 390 | 240 | 140 | 138 |

Rayon yarn waste (1 Kg) was finely divided and hydrolyzed in an aqueous solution of hydrochloric acid having a concentration of 0.3, 0.6 or 1.2% (bath ratio=13) at 100° C. for 40 minutes. The hydrolyzed product was washed with warm water or washed by filtration or decantation. When the 0.6% or 1.2% aqueous solution was used, the washed hydrolyzed product was treated with a colloid mill (25 clearances per 100 mils). The hydrolyzed product was then subjected to suction filtration, air-dried and pulverized by the same jet mill as described above. In this manner, samples (M), (N), (O), (P) and (Q) having properties shown in Table 7 were obtained.

Table 7

|  | Sample (M) | Sample (N) | Sample (O) | Sample (P) | Sample (Q) |
|---|---|---|---|---|---|
| Hydrochloric acid concentration (%) | 0.3 | 0.6 | 0.6 | 1.2 | 1.2 |
| Colloid mill | not used | not used | used | not used | used |
| Apparent specific volume (cc/g) | 2.01 | 1.92 | 1.89 | 1.76 | 1.74 |
| Tapping apparent specific volume (cc/g) | 1.83 | 1.74 | 1.63 | 1.42 | 1.35 |
| Repose angle (degrees) | 42 | 40 | 38 | 38 | 39 |
| 200-Mesh sieve residue (% by weight) | 10 | 9.2 | 7.3 | 5.1 | 2.5 |
| DP | 70 | 68 | 67 | 55 | 54 |

Powdery mixes shown in Table 8 were prepared by using the above microcrystalline cellulose samples (E) to (Q) as the excipient and commercially available pharmacopoeial powdery ascorbic acid (repose angle=58° to 60°) as the main ingredient.

Table 8

| Excipient Sample | Amount of Excipient | Amount of Main Ingredient |
|---|---|---|
| (E) | 600 g (20%) | 2400 g (80%) |
| (F) | 600 g (20%) | 2400 g (80%) |
| (G) | 600 g (20%) | 2400 g (80%) |
| (H) | 600 g (20%) | 2400 g (80%) |
| (I) | 600 g (20%) | 2400 g (80%) |
| (J) | 600 g (20%) | 2400 g (80%) |
| (K) | 600 g (20%) | 2400 g (80%) |
| (L) | 600 g (20%) | 2400 g (80%) |
| (M) | 600 g (20%) | 2400 g (80%) |
| (N) | 600 g (20%) | 2400 g (80%) |
| (O) | 600 g (20%) | 2400 g (80%) |
| (P) | 600 g (20%) | 2400 g (80%) |
| (Q) | 600 g (20%) | 2400 g (80%) |

Each of the so prepared powdery mixes was charged in a hopper and a preliminarily closed discharge port was then opened and the state of flow-out of the powdery mix was examined.

In case of the excipients (E), (G), (J), (K), (M), (N), (O), (P) and (Q), all of the charged powder substantially flowed out by its own weight. In case of the excipients (F), (H) and (L), the powder flowed out when gently vibrated, but in case of the excipient (I), bridging was often caused in the hopper and no free flow-out was observed.

EXAMPLE 5

The filling test was carried out by using an encapsulating machine ZANASI LZ-64 and capsules No. 3. As the powder to be encasulated, there were used an excipient sample alone and a powdery mix comprising 500 g of pulverized aspirin (repose angle=60°), 500 g of the excipient sample 5 g of magnesium stearate. Obtained results are shown in Tables 9 and 10. More specifically, results obtained when the filled weights were uniformalized are shown in Table 9, and results when the filled weights were not particularly uniformalized and the powders were freely filled are shown in Table 10.

Table 9

| Excipient Sample | Filled Weight Dispersion (δ mg) | |
|---|---|---|
|  | excipient alone (average filled weight = 165 ± 5 mg) | powdery mix (average filled weight = 190 ± 10 mg) |
| (I) | 4.3 | 7.3 |
| (J) | 2.0 | 3.2 |
| (K) | 1.9 | 3.0 |
| (L) | 2.2 | 4.0 (slight creaking) |
| (P) | 1.6 | 2.7 |
| (Q) | 2.3 | 3.9 (slight creaking) |

Table 10

| Excipient Sample | Filled Weight (mg) | |
|---|---|---|
|  | excipient alone | powdery mix |
| (I) | 148 | 181 |
| (J) | 160 (control) | 190 (control) |
| (K) | 185 | 196 |
| (L) | 212 | 219 (slight creaking) |
| (P) | 220 | 225 |
| (Q) | 219 | 224 (slight creaking) |

In case of the excipients (J), (K) and (P) where the filled weight dispersion was small as shown in Table 9, even if the filling speed was elevated (from 700 capsules per hour to 10000 capsules per hour), the filled weight dispersion could be maintained at a sufficiently low level. In case of the excipients (L) and (Q) where the spindle creaked because of the presence of large quantities of fine particles, if the filling speed was elevated, creaking became conspicuous and the filled weight dispersion became large.

Sample capsules shown in Table 9 were allowed to stand still at a temperature of 40° C. and a relative humidity of 72% for 2 weeks, and the moisture absorption after this accelerated test and the disintegration time before and after the accelerated test were determined to obtain results shown in Table 11. Water maintained at 37° C. was used for measuring the disintegration time. Incidentally, data shown in Table 11 are those obtained with respect to the powdery mix-filled capsules.

Table 11

| Excipient Sample | Moisture Absorption* % | Disintegration Time (minutes) | |
|---|---|---|---|
|  |  | before test | after test |
| (I) | 2.67 | 24.0 | >30 |
| (J) | 2.48 | 5.0 | 5.3 |
| (K) | 2.40 | <5.0 | <5.0 |
| (L) | 2.37 | <5.0 | <5.0 |

Table 11-continued

| Excipient Sample | Moisture Absorption* % | Disintegration Time (minutes) before test | Disintegration Time (minutes) after test |
| --- | --- | --- | --- |
| (P) | 2.36 | <5.0 | <5.0 |
| (Q) | 2.36 | 15.0 | 15.7 |

*the amount of moisture absorbed in the capsule per se was excluded.

EXAMPLE 6

Commercially available pharmacopoeial crystalline ascorpic acid was pulverized by a crusher to obtain fine powder having a size not exceeding 40μ. This powder had a repose angle as large as 53° and it was sticky and cohesive and poor in the flowability.

Pharmaceutical compositions having a recipe shown in Table 12 were prepared by using this pulverized ascorbic acid as the main ingredient and microcrystalline cellulose shown in Table 13 and they were subjected to direct compression in the same manner as described in Example 1 to obtain results shown in Table 14 (average tablet weight x=250 mg±10 mg).

Table 12

| Recipe No. | Main Ingredient (g) | Microcrystalline Cellulose (g) | Crystalline Lactose (g)* | Magnesium Stearate (g) | Content (%) of Mycrocrystalline Cellulose |
| --- | --- | --- | --- | --- | --- |
| 1 | 500 | 200 | 295 | 5 | 20 |
| 2 | 650 | 130 | 215 | 5 | 13 |
| 3 | 650 | 180 | 165 | 5 | 18 |
| 4 | 690 | 250 | 55 | 5 | 25 |

*DMV #200

Table 13

| | Microcrystalline Cellulose | | | |
| --- | --- | --- | --- | --- |
| | Sample (R) | Sample (S) | Sample (T) | Sample (U) |
| Average Degree of Polymerization | 180 | 200 | 130 | 40 |
| Apparent Specific Volume (cc/g) | 2.78 | 3.30 | 1.96 | 1.40 |
| Repose Angle (degrees) | 41 | 47 | 35 | 34 |
| 200-Mesh Sieve Residue (% by weight) | 22 | 22 | 17 | 5 |
| Tapping Apparent Specific Volume (cc/g) | 1.90 | 2.41 | 1.58 | 1.32 |

Table 14

| Run No. | Recipe No. | Microcrystalline Cellulose Sample | Repose Angle (degrees) of Powdery Mix | Tablet Weight Dispersion (%) | Tablet Hardness (Kg) |
| --- | --- | --- | --- | --- | --- |
| 1 | 1 | (R) | 39 | 1.5 | 4.3 |
| 2 | 1 | (S) | 47 | 3.5 | 4.8 |
| 3 | 1 | (T) | 39 | 1.4 | 4.0 |
| 4 | 1 | (U) | 39 | 1.2 | capping |
| 5 | 2 | (R) | 49 | 3.9 | 3.4 |
| 6 | 2 | (S) | 50 | 6.0 | 3.6 |
| 7 | 2 | (T) | 48 | 3.7 | 3.3 |
| 8 | 2 | (U) | 47 | 3.5 | capping |
| 9 | 3 | (R) | 40 | 1.7 | 4.3 |
| 10 | 3 | (S) | 47 | 3.7 | 4.7 |
| 11 | 3 | (T) | 40 | 1.3 | 4.1 |
| 12 | 3 | (U) | 39 | 1.1 | capping |
| 13 | 4 | (R) | 45 | 2.0 | 4.8 |
| 14 | 4 | (S) | 50 | 5.2 | 5.0 |
| 15 | 4 | (T) | 41 | 1.5 | 4.7 |
| 16 | 4 | (U) | 42 | 1.4 | capping |

Notes:
[1]The rotation number of the turn table was 30 rpm.
[2]The tablet hardness was the maximum hardness.

As will be apparent from the results shown in Table 14, only runs Nos. 1, 3, 9, 11, 13 and 15 gave satisfactory tablets. Namely, only when microcrystalline cellulose meeting the requirements specified in the present invention was used, satisfactory tablets were obtained. From the results shown in Table 14, it will readily be understood that in case of a main ingredient having a respose angle larger than 50° and being poor in the flowability, when the amount of microcrystalline cellulose of the present invention is at least 10% by weight if the main ingredient content is lower than 65% by weight or when the amount of microcrystalline cellulose of the present invention is at least 15% by weight if the content of the main ingredient content is 65% by weight or higher, direct compression can be accomplished advantageously with much reduced unevenness of the tablet weight.

EXAMPLE 7

Four pharmaceutical compositions having a recipe shown in Table 15 were separately blended for 30 minutes in a 5-liter capacity V-blender. Then, each composition was transferred into a 10-liter capacity kneader and a predetermined amount of a binder solution was added thereto. The resulting slurry was fed to a lateral type extruder and extruded through a screen having a mesh size of 1 mm to obtain wet granules. The granules were dried for 10 hours with hot air maintained at 60° C. to reduce the water content in the granules to about 2%, and then, the dried granules were passed through 12-mesh sieve and 60-mesh sieve, Thus, four kinds of dry granules were obtained When these dry granules were subjected to the disintegration test (n=6) according to the method specified in 8th Revised Japanese Pharmacopeia JP, it was found that the disintegration times were 3.1 minutes, 10.6 minutes, 2.5 minutes and 2.2 minutes, respectively. Further, 10 g of the dry granules were sealed in a Kayagski-type tablet abrasion tester and the tester was rotated for 20 minutes, and then, the tested granules were passed through a 60-mesh sieve and the amount of dust formed was determined. It was found that the amounts of dust were 2.1%, 1.8%, 2.0% and 4.3%, respectively.

Table 15

| Recipe No. | Microcrystalline Cellulose Sample | Amount Added (g) of Microcrystalline Cellulose | Amount (g) of Lactose* for Ordinary Use | Amount Added (g) of 1 % Solution of Methyl Cellulose as Binder |
| --- | --- | --- | --- | --- |
| 1 | (R) | 400 | 1600 | 1600 |
| 2 | (S) | 400 | 1600 | 1760 |
| 3 | (T) | 400 | 1600 | 1550 |
| 4 | (U) | 400 | 1600 | 1500 |

*lactose for ordinary use was used as a substitute for a water-soluble main ingredient.

In case of recipe No. 2, when the slurry was laterally extruded, slight creaking was caused and the granules split slightly. In case of recipe No. 4, slight separation of water was observed. In case of recipes No. 1 and 3, extrudability was excellent.

EXAMPLE 8

To the granules obtained in Example 7 was added magnesium stearate in an amount of 1.0% by weight based on the total weight of the granules and magnesium stearate and tablets were prepared from the mixture under the same tableting conditions as described in Example 1. Properties of the obtained tablets are shown in Table 16.

Table 16

| Recipe No. | Tablet Hardness (Kg) | Disintegration Time (minutes) | Wear Rate (%) | Remarks |
|---|---|---|---|---|
| 1 | 7.8 | 5 | 1.9 | |
| 2 | 8.2 | >12 | 1.5 | |
| 3 | 7.6 | 3 | 1.8 | |
| 4 | 3.2 | — | 12.3 | capping |

EXAMPLE 9

Commercially available pharmacopeial phenacetin was pulverized for 20 minutes by a crusher to obtain a 60-mesh passable main ingredient (respose angle=49°).

Seven powdery mixes were prepared by mixing 600 g of this main ingredient with 5 g of magnesium stearate and 395 g of corn starch, 100-mesh passable lactose, calcium phosphate, methyl cellulose (MC), polyvinyl pyrrolidone (PVP), lowly substituted hydroxypropyl cellulose (l-HPC) or microcrystalline cellulose (R) shown in Table 13 as an excipient and/or binder.

Tablets were prepared from these powdery mixes according to the direct compression method described in Example 1. Obtained results are shown in Table 17.

Table 17

| Additive | Weight Dispersion (%) | Hardness (Kg) | Disintegration Time (minutes) | Wear Rate (%) |
|---|---|---|---|---|
| Corn starch | 4.3 | capping | — | — |
| Lactose 100% | 2.1 | 0.0 | — | — |
| Calcium phosphate | 2.4 | 3.0 | >20 | 8.0 |
| MC | 5.9 | 4.1 | 15 | 4.3 |
| PVP | 7.8 | 4.5 | 12 | 5.1 |
| l-HPC | 12.3 | 6.2 | 7 | 2.3 |
| Sample (U) | 1.6 | 9.8 | <1 | 0.9 |
| Control (Avicel pH-101) | 2.5 | 7.1 | 8 | 0.7 |

From the results shown in Table 17, it will readily be understood that tablets prepared from a pharmaceutical composition comprising microcrystalline cellulose of the present invention have a high hardness and a short disintegration time with much reduced weight unevenness and therefore, they are very excellent in properties required of tablets.

The claims defining the invention are as follows:

1. An exipient consisting essentially of a microcrystalline cellulose having an average degree of polymerization of 60 to 375 and obtained through acid hydrolysis or alkaline oxidative degradation of a cellulosic substance selected from linters, pulps and regenerated fibers, said microcrystalline cellulose being a white cellulosic powder having an apparent specific volume of 1.6 to 3.1 cc/g, and a repose angle of 35 to 42°.

2. An excipient as set forth in claim 1 wherein the average degree of polymerization is 70 to 180 and the apparent specific volume is 1.9 to 2.8 cc/g.

3. An excipient as set forth in claim 1 wherein the repose angle is 38 to 42°.

4. A pharmaceutical composition comprising a pharmaceutically active ingredient and an excipient which consists essentially of a microcrystalline cellulose having an average degree of polymerization of 60 to 375 and obtained through acid hydrolysis or alkaline oxidative degradation of a cellulosic substance selected from linters, pulps and regenerated fibers, said microcrystalline cellulose being a white cellulosic powder having an apparent specific volume of 1.6 to 3.1 cc/g, and a repose angle of 35 to 42°.

5. A pharmaceutical composition as set forth in claim 4 wherein said excipient is present in an amount of 2 to 40% by weight based on the pharmaceutical composition.

6. A pharmaceutical composition as set forth in claim 4 wherein said excipient is present in an amount of at least 10% by weight based on the pharmaceutical composition.

7. A pharmaceutical composition as set forth in claim 6 wherein said pharmaceutically active ingredient has a repose angle not larger than 50°.

8. A pharmaceutical composition as set forth in claim 6 wherein said pharmaceutically active ingredient has a repose angle of at least 50° and is present in an amount of not higher than 65% by weight based on the pharmaceutical composition.

9. A pharmaceutical composition as set forth in claim 4 wherein said excipient is present in an amount of 15 to 35% by weight based on the pharmaceutical composition, and the pharmaceutically active ingredient has a repose angle of at least 50° and is present in an amount of 65 to 85% by weight based on the pharmaceutical composition.

10. A pharmaceutical composition as set forth in claim 4 which further comprises other additives.

* * * * *

UNITED STATES PATENT AND TRADEMARK OFFICE
CERTIFICATE OF CORRECTION

PATENT NO. : 4,159,345

DATED : 26 June 1979

INVENTOR(S) : Kimihiko Takeo; Tetuya Aoyagi; Akimitsu Tamada

It is certified that error appears in the above-identified patent and that said Letters Patent are hereby corrected as shown below:

Column 4, line 28, insert a comma -- , -- after the word "excipient". Column 11, line 63, "become" should read -- became --. Column 15, line 56, Table 14, under the heading "Recipe No." insert the numeral one -- 1 --. Column 16, line 41, " , " in first occurence should read -- . --; line 42, insert a period -- . --, after the word "obtained"; line 48, "Kayagski" should read -- Kayagaki --. Column 18, line 5, "exipient" should read -- excipient --.

Signed and Sealed this

Ninth Day of October 1979

[SEAL]

Attest:

RUTH C. MASON
*Attesting Officer*

LUTRELLE F. PARKER
*Acting Commissioner of Patents and Trademarks*